United States Patent [19]

von Bernus et al.

[11] Patent Number: 4,687,992

[45] Date of Patent: Aug. 18, 1987

[54] METHOD FOR TESTING PARTS, ESPECIALLY OF NUCLEAR PLANTS, BY MEANS OF EDDY CURRENT

[75] Inventors: Ludwig von Bernus, Hemhofen; Georg Bögelein; Rudolf Waldhütter, both of Erlangen, all of Fed. Rep. of Germany

[73] Assignee: Kraftwerk Union Aktiengesellschaft, Mülheim, Fed. Rep. of Germany

[21] Appl. No.: 717,888

[22] Filed: Mar. 29, 1985

[30] Foreign Application Priority Data

Mar. 30, 1984 [DE] Fed. Rep. of Germany ....... 3411898

[51] Int. Cl.⁴ ...................... G01N 27/90; G01R 33/12
[52] U.S. Cl. .................................... 324/232; 324/220; 324/227
[58] Field of Search ........ 324/225, 227, 232, 219–221, 324/237, 238, 240–242

[56] References Cited

U.S. PATENT DOCUMENTS

| | | | |
|---|---|---|---|
| 2,992,390 | 7/1961 | De Witte | 324/220 |
| 3,437,810 | 4/1969 | Wood et al. | 324/221 X |
| 4,303,885 | 12/1981 | Davis et al. | 324/232 X |
| 4,325,026 | 4/1982 | Cooper et al. | 324/232 |

OTHER PUBLICATIONS

Davis, T. J., *Advances in Multifrequency Eddy Current Instrumentation*, BN-SA-946, Periodic Inspection of Pressurized Components Conf. Presentation, May, 1979, London, pp. 1–9.

*Primary Examiner*—Gerard R. Strecker
*Attorney, Agent, or Firm*—Herbert L. Lerner; Laurence A. Greenberg

[57] ABSTRACT

Defect detection in testing pipes, particularly in heat exchangers of nuclear reactors by means of eddy current in which interference influences due to the design are suppressed by measurements with different frequencies and the frequencies interlinked to give a signal only if there is a defect indication.

12 Claims, 2 Drawing Figures

4,687,992

METHOD FOR TESTING PARTS, ESPECIALLY OF NUCLEAR PLANTS, BY MEANS OF EDDY CURRENT

BACKGROUND OF THE INVENTION

FIELD OF THE INVENTION

The invention relates to a method for testing pipes, particularly in heat exchangers of nuclear plants, by means of eddy current where several measurements with different frequencies are made and the measuring results are interlinked with each other for suppressing design-related interference influences.

Among the design-related interference influences which have an adverse effect on the determination of defects in that they cause signals similar to faults, are counted spacers, ovalness at the beginning of a pipe elbow, deposits, the tube elbow, rolled-in portions, external baffles and flow distribution plates, etc. The interference of the tubes and components are dependent on frequency. To eliminate the influences of the interference signals, the measurements and tests are performed in sequence one after the other with different frequencies. In this way the interference signals are in the background compared to the defect signals. However, the parameters of such multiple-frequency interlinkage must be adapted to the interference signal to be suppressed. If different interference influences are present in the region to be tested, interlinkages with different sets of parameters must as a rule be used for suppressing them. The problem then consists in selecting the respectively correct set of parameters for the different interference signals which occur in the testing of a pipe sequentially in time.

SUMMARY OF THE INVENTION

The objective of the invention is to simplify the measurements by a special interlinkage of the test signals, so that automation of the defect detection in testing metallic parts is possible. This is particularly important for the inside testing of steam generator tubes in nuclear power stations because work is possible there only for short periods of time or only with remote control because of the radiation exposure.

With the foregoing and other objects in view, there is provided in accordance with the invention a method for testing pipes, particularly in heat exchangers of nuclear installations, by means of eddy current where, for suppressing interference influences due to the design, measurements with different frequencies are made and the measurement results are interlinked with each other, characterized by the feature that three signals are generated, of which the 1st signal serves for ascertaining defects in interference-free or low-frequences tube regions, the
2nd signal serves for ascertaining defects in the region of heavy interference influences, the
3rd signal serves for determining strong interference influences; these signals are continuously monitored simultaneously for a threshold value; and a defect indication is given only for one of 1 and 2 below:
1. the first signal alone
2. the first and the second signal reach their threshold value together.

Although the invention is illustrated and described herein as embodied in method for testing metallic parts, especially of nuclear plants, by means of eddy current, it is nevertheless not intended to be limited to the details shown, since various modifications and structural changes may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawing, in which.

DESCRIPTION OF THE PREFERRED EMBODIMENTS

Figure 1:
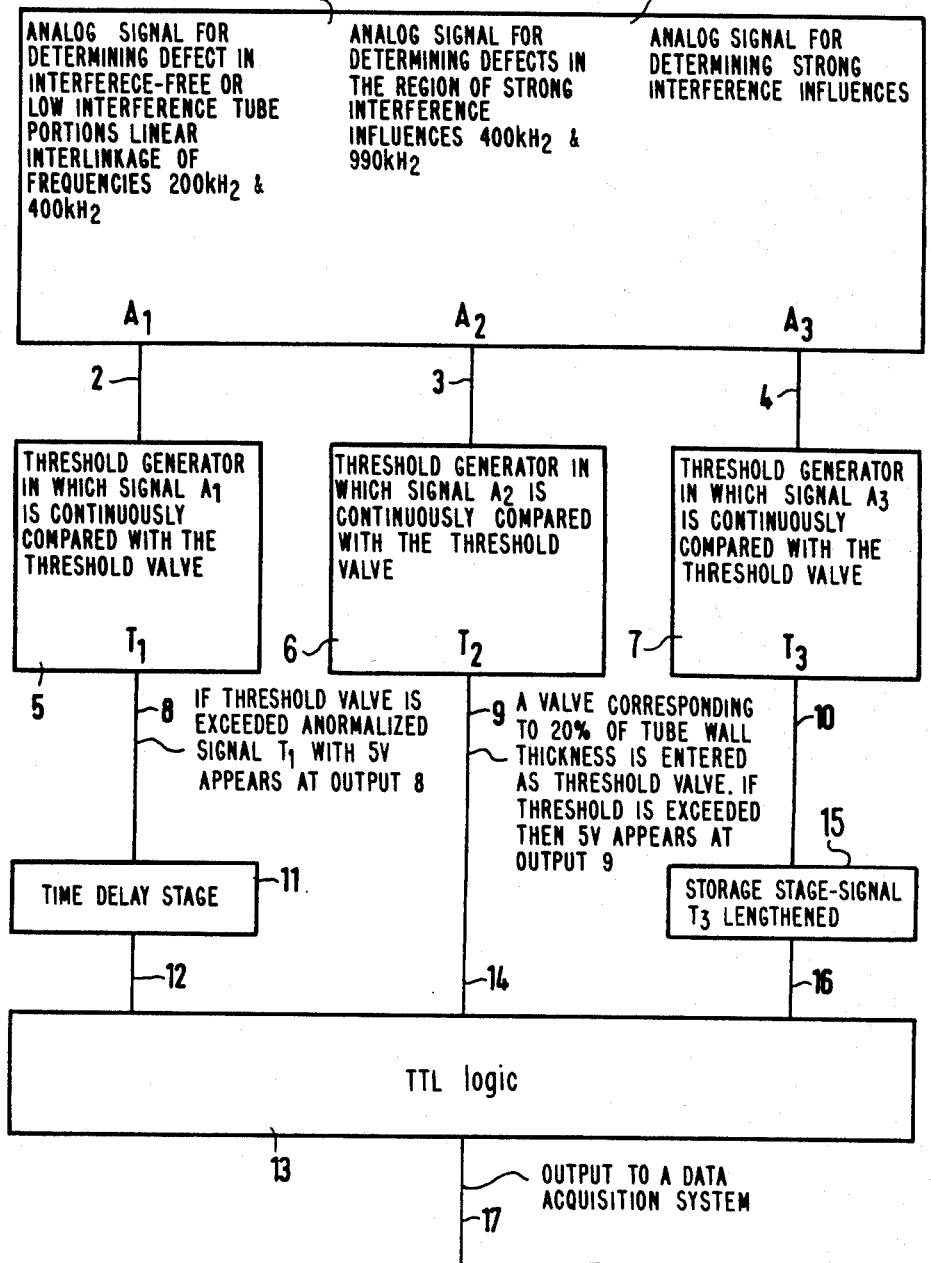
FIG. 1 is a block diagram of an equipment cabinet containing the electronic circuitry for eddy current probes which are used for the testing of steam generator tubes of a pressurized-water reactor; adjustable threshold generators in which signals are continuously compared with threshold values; a time delay stage, and a storage stage to lengthen the signal; and a TTL logic which receives input from the signals and gives the result.

According to the invention, three signals are generated, of which the

1st signal serves for determining defects in interference-free or low-interference tube portions, the
2nd signal is for determining defects in the region of strong interference influences and the
3rd signal is for determining strong interference influences; the signals are continuously and simultaneously monitored for a threshold value; and a defect is indicated only if
1. the first signal alone or
2. the first and the second signal together reach their threshold value.

In the invention a differentiation, if signal comes from a defect or from interference by the tubes, is not limited by a simple interconnection of several frequencies. Actually, three signals are generated, which are so chosen that at a test at each position a good differentiation of defect signals and interference signals is assured. The interference signals are caused by the construction of the tubes.

Three analog signals $A_1$, $A_2$, $A_3$ are therefore provided for the automated defect detection. The three analog signals A, $A_2$ and $A_3$ can be complex signals of different test frequencies or interlinked signals. The analog signals $A_1$, $A_2$ and $A_3$ are converted by discriminators into the TTL-signals $T_1$, $T_2$ and $T_3$. "TTL"=Transistor-Transistor-Logic, for a circuit composed of transistors and having a standardized signal level such as volt for example. This is generally in integrated form. The signals $T_1$, (or $A_1$) and $T_2$ (or $A_2$) serve to determine defect localization. The purpose of signal $T_1$ is to indicate defects in the interference-free region or in the region with low interference influences (for instance, deposits, spacers, Pilger effects). "Pilgereffect"=is a deviation of the inner diameter of the tube which is to be tested, that deviation resulting from the manufacture of the tube. $T_2$ is suitable for finding defects in the region of an interference type with a large amplitude (for instance, roll-in effects). $T_3$ has the purpose of indicating the presence of this interference type.

The signals $T_1$, $T_2$ and $T_3$ are then fed to the input of the TTL logic known per se and are further processed in accordance with the "Truth Table" at the end of the specification.

In realizing the invention, the precedure can advantageously be set such that the first signal is the amplitude as a complex analog value and that the imaginary part thereof is used for the threshold-value comparison. The parameters of the signal generated, for instance, as an ALS or AH mix are chosen so that all interference influences at the outside tube surface (spacer, baffle, flow distribution plate) are suppressed. The signal has a relatively high testing sensitivity and serves for finding defects in the entire tube with the exception of the rolled-in parts, since the latter leads to a false defect signal because of the high sensitivity.

"ALS"=spacer, guide plate and flow distributor plates-essentially as a generic term it is an all inclusive term for internals of a steam generator which have an effect upon the signal which occurs from the steam generator tubes during a turbulent current test. They produce a so-called mix signal which makes it difficult to recognize the error signal which is actually being sought-after.

"AH"=spacer, these spacers give off by themselves and not only in combination with ALS a mix signal from which a fault signal is to be sought out.

The frequency of the second signal is so chosen that measurements in the range of the expected interference influences are made possible. Of this value, the ratio of the real part to the imaginary part is used for the comparison with the threshold values. Defects in the region of strong interference are determined with this signal, so that one has a reduced defect sensitivity as compared with defects at the points where such interference is not present. An interference source of this type is particularly the roll-in point.

An advantageous procedure for detecting the so-called strong interference source would be to have the third signal an impedance value measured with suitable frequency, and to use the real part thereof (X-value) for the comparison with the threshold values.

In order to assure the synchronization of the signals, a time delay stage with adjustable delay time, preferably 5 to 50 ms, can be connected in series with the logic, especially in the first channel. A time delay member in the third channel can take care of an extension in time, preferably 50 to 250 ms, of this signal so that well-defined conditions prevail in the region of the entire roll-in point.

To explain the invention in greater detail, block diagrams with a TTL logic are described with the aid of the attached drawings as embodiment examples, by which the invention is realized for the automated pipe testing.

Numeral 1 designates an equipment cabinet which contains the electronic circuitry for eddy current probes which are known but not shown and which are used for the testing of steam generator tubes of a pressurized-water reactor. The three complex analog signals $A_1$, $A_2$ and $A_3$ are taken off at their respective outputs 2, 3 and 4.

Signal $A_1$ is a linear interlinkage of the frequencies 200 kHz and 400 kHz.

Signal $A_2$ is a linear interlinkage of the frequencies 400 kHz and 990 kHz.

Signal $A_3$ is the impedance of a test coil measured at 400 kHz.

Thus, the signals $A_1$, $A_2$ and $A_3$ are generated by the electronics of the eddy current probes. The signals $A_1$ and $A_2$ are linear combinations i.e. superpositions of two frequencies.

The outputs 2, 3 and 4 are connected respectively to three adjustable threshold generators 5, 6 and 7, in which the signals $A_1$, $A_2$ and $A_3$ are continuously compared with the following threshold values.

The so-called Y-threshold 5 for the imaginary part of signal $A_1$ corresponds to the indication of the testing error $3\times0$, $3\times100\% -12$ dB. If this value is exceeded, a normalized signal $T_1$ with 5 V appears at the output 8. $3\times0.3\times100\% -12$ dB means that signal which originates in a test tube comparable to the tested one, if three bores are provided in this test tube disposed uniformly at the periphery and having a diameter of 0.3 mm and 100% depth (i.e. a through bore).

To obtain the so-called angle threshold, a value corresponding to a defect depth of 20% of the tube wall thickness is entered from the ratio of real part to imaginary part. If the threshold value is exceeded, the signal $T_2$ normalized to 5 V appears at the output 9.

The so-called X-threshold 7 for recognizing a rolled-in spot or a similarly great disturbance, responds to the real part of the analog signal $A_3$. The signal $A_3$ is excited with 400 kHz. The threshold for the normalized signal $T_3$ appearing at the output 10 is set so that the rolled-in spot is recognized reliably in all cases.

In order to assure the synchronization of the signals $T_1$ and $T_2$, the output 8 is connected with the input 12 of a TTL logic 13 by a time delay element 11. The delay time is about 25 ms (milliseconds), corresponding to a tube length of 5 mm.

The output 9 leads directly to the input 14 of the TTL logic 13.

In order that at the whole rolled-in operation equally defined conditions exist, and the signal $T_3$ is available for the whole test procedure in the same way, the output 10 leads to a storage stage 15, by which the signal $T_3$ is continued for to about 250 ms so that the input 16 of the TTL logic is at least loaded for 250 milliseconds as the X-threshold 7 is triggered.

The TTL logic 13 reports at its output 17, to which a data acquisition system, for instance, a magnetic tape or the like is connected, a defect according to the interlinkage of the "Truth Table" given at the end of the specification. This defect is associated in the data acquisition system with a tube region which is fed, via a distance pickup, not shown, to an eddy current probe, for instance, via a time-dependent probe feed.

Figure 2:
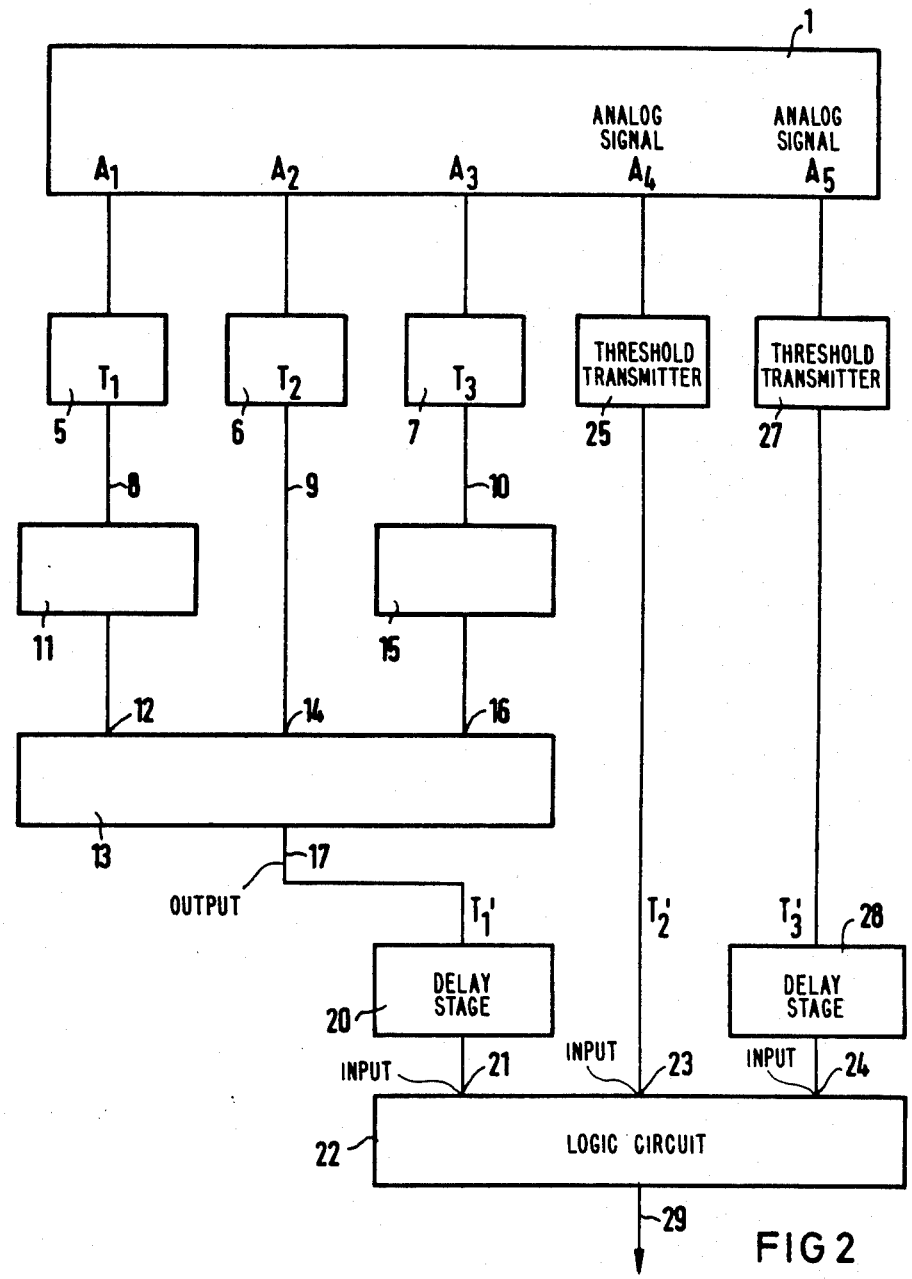
FIG. 2 is similar to FIG. 1 but for the purpose of distinguishing two types of interference several signal interlinkage logic currents are connected.

If more than two types of interference in the tubes must be distinguished, several signal interlinkage logic circuits are connected in series according to FIG. 2. The output 17 of the TTL logic 13 is then connected optionally to the input 21 of a following logic 22 via a delay stage 20. The inputs 23 and 24 of the logic 22 are then available for detecting a further type of interference and for localizing defects at this point. Such a type of interference can stem, for instance, from the deposits called "dents". To this end, a signal $A_4$ of the equipment cabinet 1 is fed to the input 23 via a threshold transmitter 25. A signal $A_5$, a 50-kHz analog signal, arrives at the input 24 via a threshold transmitter 27 and a storage device 28 with a delay of 25 ms. A data acquisition system is connected to the output 29.

The invention has the advantage that an interference source can be recognized precisely, independently of a frequently too inaccurate measurement of the coil location by the distance pickup of the manipulator. The test range in which the multi-frequency interlinkage suitable for this interference is used, can thereby be brought into coincidence with the range of the interference indication.

TRUTH TABLE

| Explanation | Inputs | | | Output |
|---|---|---|---|---|
| | T1 | T2 | T3 | |
| Defect in the rolled-in part or very large defect | yes | yes | yes | yes |
| Large defect in the vicinity of the roll-in | yes | yes | no | yes |
| Small defect not in the vicinity of the roll-in | yes | no | no | yes |
| Roll-in without defect | yes | no | yes | no |
| Interference | no | yes | yes | no |
| Interference | no | yes | no | no |
| Interference | no | no | yes | no |
| Defect-free tube region outside the roll-in | no | no | no | no |

There are claimed:

1. Method for testing tubes to determine tube defects, particularly in heat exchangers of nuclear installations, by means of eddy current, and suppressing interferences due to design and construction of the tubes to be tested, which comprises:
generating three eddy current signals designated 1st signal, 2nd signal and 3rd signal with different frequencies in a tube to be tested, the
1st signal being generated in interference-free or low interference tube regions to ascertain defects in such tube regions, the
2nd signal being generated in a tube region which has construction-caused interferences to ascertain defects in said region in the presence of strong interference influence, and the
3rd signal being generated in the tube to determine strong interference quantities therein in said region of strong interference influence, continuously, separately and simultaneously monitoring said three signals, comparing each signal with a predetermined threshold value, obtaining output signals designated 1st output signal, 2nd output signal and 3rd output signal corresponding to 1st signal, 2nd signal and 3rd signal if the predetermined threshold values are exceeded, and indicating a defect in the tube from said output signals upon the occurrence of one of (a) and (b) below:
(a) only the 1st signal reaches its threshold and the 1st output signal is obtained,
(b) the 1st and 2nd signals reach their thresholds together and the 1st and 2nd output signals are obtained.

2. Method according to claim 1, wherein the first signal is the amplitude of a complex analog value and the imaginary part thereof is used for comparison with the threshold value.

3. Method according to claim 1, wherein the second signal is a complex analog value adapted to the expected interference quantity, and the ratio of the real part to the imaginary part thereof is used for comparison with the threshold value.

4. Method according to claim 2, wherein the second signal is a complex analog value adapted to the expected interference quantity, and the ratio of the real part to the imaginary part thereof is used for comparison with the threshold value.

5. Method according to claim 1, wherein the third signal is an impedance value measured with a suitable frequency, and the real part (X-value) is used for comparison with the threshold value.

6. Method according to claim 2, wherein the third signal is an impedance value measured with a suitable frequency, and the real part (X-value) is used for comparison with the threshold value.

7. Method according to claim 3, wherein the third signal is an impedance value measured with a suitable frequency, and the real part (X-value) is used for comparison with the threshold value.

8. Method according to claim 1, wherein the 1st output signal is delayed by 5 to 50 ms.

9. Method according to claim 1, wherein the 3rd output signal is lengthened by 50 to 250 ms.

10. Method according to claim 1, wherein the defect indication is used as the first of three signals in which a second output signal serves for ascertaining defects in the region of another strong interference influence, and third output signal serves for determining this other strong interference influence.

11. Method according to claim 10, wherein the 3rd signal and the third signal of of another strong interference influence are generated with different frequencies.

12. Method according to claim 1, wherein the 1st signal and the 2nd signal are each generated of multi-frequency interlinkage.

* * * * *